(12) United States Patent
Freudenthal

(10) Patent No.: US 8,628,540 B2
(45) Date of Patent: Jan. 14, 2014

(54) SNARE MECHANISM FOR SURGICAL RETRIEVAL

(75) Inventor: Franz Freudenthal, La Paz (BO)

(73) Assignee: PFM Medical AG, Cologne (DE)

( * ) Notice: Subject to any disclaimer, the term of this patent is extended or adjusted under 35 U.S.C. 154(b) by 893 days.

(21) Appl. No.: 12/288,972

(22) Filed: Oct. 24, 2008

(65) Prior Publication Data

US 2009/0112244 A1 Apr. 30, 2009

Related U.S. Application Data

(60) Provisional application No. 61/000,307, filed on Oct. 25, 2007.

(51) Int. Cl.
*A61B 17/24* (2006.01)
(52) U.S. Cl.
USPC .......................................................... 606/113
(58) Field of Classification Search
USPC .................... 606/113, 114, 159, 167, 200; 600/104–107
See application file for complete search history.

(56) References Cited

U.S. PATENT DOCUMENTS

| | | | |
|---|---|---|---|
| 5,171,233 A | 12/1992 | Amplatz | |
| 5,562,678 A * | 10/1996 | Booker | 606/113 |
| 6,007,546 A | 12/1999 | Snow et al. | |
| 2002/0188262 A1 * | 12/2002 | Abe | 604/326 |
| 2005/0096506 A1 | 5/2005 | Nishtala et al. | |
| 2005/0209609 A1 * | 9/2005 | Wallace | 606/113 |
| 2006/0129166 A1 | 6/2006 | Lavelle | |
| 2007/0118165 A1 | 5/2007 | DeMello et al. | |

FOREIGN PATENT DOCUMENTS

| | | |
|---|---|---|
| DE | 37 17 657 A1 | 8/1988 |
| DE | 37 17 657 A1 | 12/1988 |
| DE | 195 14 534 A1 | 10/1996 |
| DE | 195 14 534 C2 | 2/1997 |
| DE | 198 42 420 C2 | 12/2000 |
| DE | 198 42 520 C2 | 12/2000 |
| DE | 199 64 093 A1 | 11/2001 |
| DE | 20 2007 006 619 U1 | 8/2007 |
| EP | 0997 106 B1 | 2/2005 |
| EP | 1 404 237 B1 | 9/2007 |
| WO | WO 00/16703 A | 3/2000 |
| WO | WO0016703 A1 * 3/2000 ............ A61B 17/22 |
| WO | WO 03/002006 A | 1/2003 |
| WO | WO 2005/011506 A | 2/2005 |
| WO | WO 2005/034774 A | 4/2005 |
| WO | WO 2006/039216 A | 4/2006 |
| WO | WO 2007/000452 A3 | 1/2007 |

\* cited by examiner

*Primary Examiner* — Ryan Severson
*Assistant Examiner* — Rachel S Papeika
(74) *Attorney, Agent, or Firm* — Grossman, Tucker, Perreault & Pfleger, PLLC

(57) ABSTRACT

A snare device for capturing an object or for cutting tissue in the body of a human or animal. The device employs at least one twisted loop of memory shaped material housed in and movable relative to a hollow member such as a catheter. The device and method of employment is particularly well adapted for retrieving objects from internal body cavities and cutting tissue therein.

16 Claims, 12 Drawing Sheets

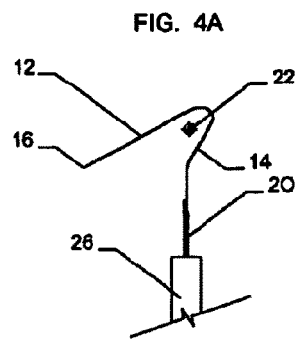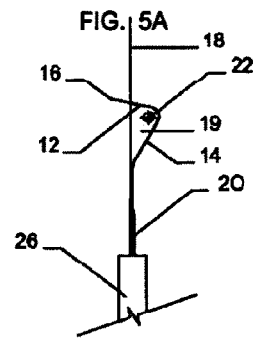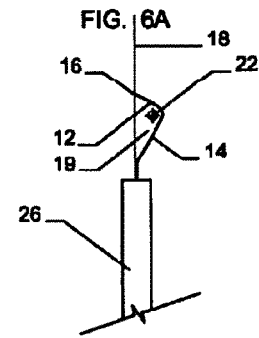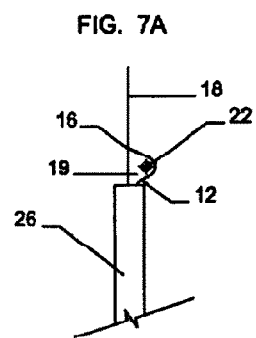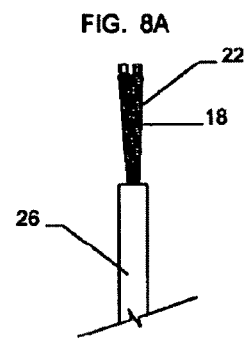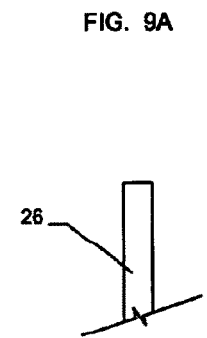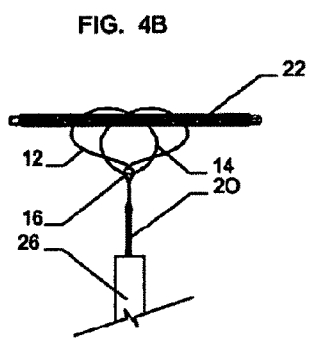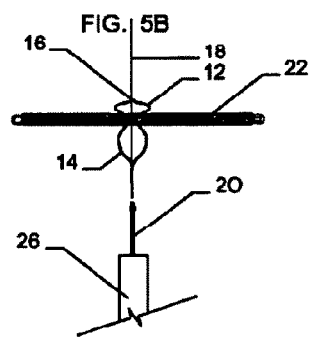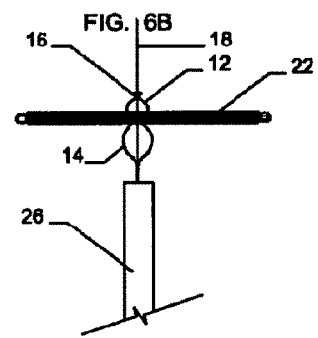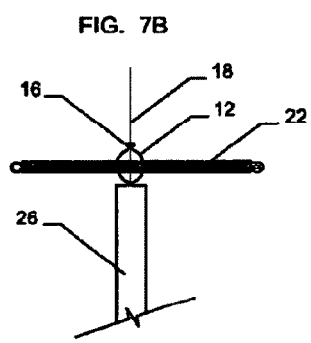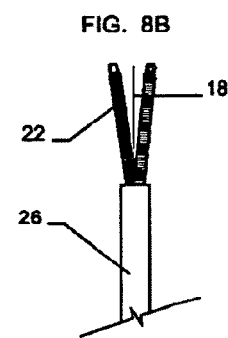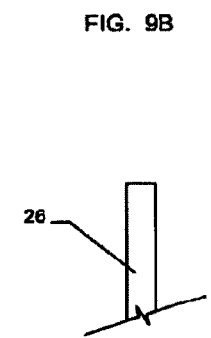

SNARE MECHANISM FOR SURGICAL RETRIEVAL

This application claims the benefit of U.S. Provisional Application No. 61/000,307 filed on Oct. 25, 2007 and incorporated herein in its entirety by reference. This invention claims prior The invention relates to a snare device for capturing an object and/or for cutting a tissue comprising at least one twisted loop of memory shaped material, the loop being housed in and movable relative to a hollow member, especially a catheter to be deployed and retracted into the hollow member, and to a method for retrieving an object from a human or animal body employing such a snare device and a method for cutting a tissue by use of such a snare device. The disclosed device relates to retrieval devices for use in surgery. More particularly, the disclosed device relates to a design and assembly for intravascular object retrieval or for retrieving objects from internal body cavities. Further, the device also relates to cutting a tissue within a human or animal body.

FIELD OF THE INVENTION

Background of the Invention

Evolving medical procedures and new technologies have provided medical professionals with an ever widening array of procedures and equipment for repair and assessment of vascular problems in patients. Most such modern investigative and repair devices employ catheters and guide wires which are maneuvered through the femoral artery and communicated to the heart for viewing and repairing unnatural blockages or openings present. Diagnosing the problem with a patient involves generally the injection of radiological dyes to ascertain the current or actual state of the medical problem. Subsequently, repair can involve any number of procedures such as installing stents or PFO closure devices.

As in any art where structural and other mechanical devices are positioned remotely to the control device therefore, on occasion a loss of control of the maneuvered device or unexpected dismounting thereof can leave any number of foreign objects dangerously loose in the vascular system of the patient. Such devices may include loose or detached PFO closure components, loose or detached stents, diagnostic electrodes, broken wires, and any number of loose components. As the technology and equipment evolves for vascular intervention, so does the number of potential loose objects which might endanger the patient.

If a loose object or component is detected, a number of methods are conventionally employed to retrieve it. A first approach to retrieval is surgery on the patient. This choice is not favored since an incision is formed proximate to the site of the loose object and subsequently the surgeon must cut away surrounding tissue to reach the loose object.

As can be discerned, this would not be the plan of choice to most physicians if other means were available to retrieve the object. This is because cutting away the tissue of the organ in question causes injury to the patient which subsequently must be repaired by sutures. Damage to the tissue being dissected is highly possible as is the potential for dissecting important nerves or unseen blood vessels. The subsequent healing process can take many weeks and further the patient conventionally must undergo general anesthesia which in itself has risks to the patient. This approach is expensive due to the use of operating rooms and the patient recovery time.

A currently more favored approach is seeking out the loose object using a catheter communicated through the appropriately sized blood vessels for a removal and recovery of the object. Or, the device may be inserted through a tissue wall to the site of the recovery. Since the patent is in a cath-lab or similar setting, general anesthesia is not necessary and because the surgeon need not make tissue incisions, the risk to the patient is lessened as is recovery time.

Conventionally, in this type of retrieval action, a catheter, with some type of object engaging distal end or tip is communicated through the appropriated blood vessel to the site of the loose stent, tool, or other loose object. In the same manner as implant viewing of the site, a fluoroscope is employed to view the distal end capture device approaching and engaging the loose object. Once sufficiently proximate to the loose object, the capture device is positioned to engage the loose object using the fluoroscope. Once the engaging distal end of the catheter is secured to the targeted object, the catheter is translated from the vascular system pulling the object along with it from the body.

However, conventional object engaging tools can themselves cause problems or be very hard to employ. One such engagement component uses a hook-shaped tool which, much like fishing, is positioned to hook onto the loose object and once hooked up, the object is dragged from the vascular system. Hooks, however, can become dislodged as they frequently depend on the force of the wire to which they are engaged during removal, to stay engaged to the object. A reverse translation of the retrieval wire can dislodge the hook. Further, hooks do not fare well in a reverse engagement of the loose object since when pulled by their engaged guide wire, the hook will reverse itself and can become dislodged.

Further, hooks by their nature are designed to engage things when their lead wire is pulled with force. The hook can therefore easily miss its target and engage surrounding tissue which will cause damage thereto and could require surgery for removal. Finally, while hooks work well on larger objects and objects with passages to engage the hook, short and small objects relative to the hook size can be hard to engage and very easy to dislodge.

Yet another conventionally employed object retrieval device employs jaws such as those on forceps to clamp onto the loose object at the distal end of a catheter and control wire for the jaws. Because of the mechanics involved in rotating jaws around an axis, the size of these devices can be much too large for many vessels and much like pliers or vice-grips, the jaws only hold the object so long as the force of the grip exceeds the force of dragging it from the body.

A more recent device employed for grasping loose objects in the body or vascular system is a snare or open loop or lasso. These devices ensnare around the loose object and are then closed or constricted to a forced grip on the object by translation of a control wire in the catheter.

An example of a loop device for object retrieval is taught in U.S. Pat. No. 5,171,233, (Amplatz) which discloses a catheter engaged loop from the distal end of a catheter. This device is maneuvered to the site of the loose object and then the planar loop is deployed in a plane between 45 and 135 degrees relative to the axis of a proximal member comprising two parallel wires and over the end of the object being retrieved. The shape memory material forms a loop intended to encircle the object and then the loop wires can be translated back into the axial cavity in the catheter thereby tightening the loop around the object and pulling it against the distal end of the catheter in a tight fit for retrieval. While the engagement may be tight, this can cause a problem during removal as the catheter must negotiate many turns. If the object is in a fixed engagement against the distal end of the catheter at an odd angle to the center axis of the catheter, maneuvering around tight turns becomes a problem such as by potential injuries to vascular tissue from dragging the object at such an angle out of the body.

Further, the cited preferred ninety-degree deployment of the planar loop in its attempt to encircle an object is severely impeded if the object, such as a stent, is engaged to wall tissue in the artery. This can make it difficult or impossible to actually engage the loose object. As such, an unmet need exists for a snare type capturing device for retrieval of loose objects in the vascular system or other parts of the body. Such a device should be capable of engagement with the many types of objects which can become loose in the body.

DE 198 42 520 C2 discloses a device for grasping objects, in particular foreign objects, agglomerates, stones or other organic deposits or accumulations from human or animal vessels or body cavities. The device has an elongate proximal section and a distal section which is provided with a noose, the noose consisting of a flexible elastic material. The device has an at least partly two-ply noose. The device can be converted from this initial configuration into a second configuration in cooperation with an elongate tubular device at least partly enveloping the instrument or device, where the noose is angled at least in its initial configuration at a predetermined angle from the long axis of the elongate proximal section. According to this prior art one noose part is closed and the other is formed either partly surrounding the latter or partly inscribing in the latter. Because of the double-surrounding of objects or particles these can be have a variety of dimensions and shapes and can be held more firmly as compared to the instrument disclosed in DE 195 14 534 C2, when retracted into a catheter, The latter prior art discloses a snare device with an elongate proximal part and a distal part in the shape of a snare of flexible super-elastic material. In the side view of this instrument the distal part is bent relative to the axis going through the longitudinal proximal part bent first to one side and afterwards in the shape of a U to the opposite side. There is only one open or closed snare provided according to this prior art.

A further instrument for grasping objects from the inside of a human or animal body is disclosed in DE 37 17 657 A1 wherein a snare is provided which is retractable into a tubus and because of its self-elasticity opens when pushed out of the tubus. This snare or loop can be closed by use of a pulling wire which is provided at the snare or loop. By pulling the pulling wire the opening of the loop or snare is partly closed in order to hold an object in the loop. The pulling wire is, thus, connected to the loop in the longitudinal direction of the loop by further using a transverse wire connected transverse to the loop inside of the same.

Further, EP 1 404 237 B1 discloses a device for grasping objects from a human or animal body, comprising a first part for grasping the object and a second part for holding the grasped object wherein the first part comprises at least two branches where the distal ends of at least some of the branches are provided with snares running from the branches and wherein the snares circumscribe the second part of the device mentioned as an extraction basket. At least some of the distal ends of the snares are intertwisted to build a net with a cell-structure which can hold the grasped object inside the second part of the extraction basket.

DE 20 2007 006 619 U1 discloses a medical instrument with an operable snare type device for grasping and holding of tissue at the distal end of a handle wherein the snare type device is provided as a cutting device for cutting the grasped tissue. In a first embodiment the snare is provided as a cutting wire, the wire having a sharp edge for cutting. The snare is retracted into a handle and can be deployed out of it. It is further disclosed to provide a monopolar cutting instrument powered by a high frequency current. Therefore, this prior art document discloses to cut a tissue either by use of a cutting wire or by use of high frequency current the cutting wire is delivered with.

A similar device is the polypectomy snare as disclosed in WO 2007/000452 A3. A surgical cutting device comprises a traction/push element which is guided into a bushing and used to transfer a traction or pushing force from an actuation device arranged on one end of the bushing to a loop which is arranged on the other end of the bushing. By this force the loop may be arranged in a storage position wherein the loop lies in an extended position in the bushing and in a user position wherein the loop lies in an expanded opening in front of the bushing. The loop itself is formed by two V-shaped expansion limbs in the user position, partially in and in front of the bushing. The limbs are resistant to bending at least in the direction which is transverse in relation to the opening plane as a loop arc which can be connected to the respective free ends of the expansion limb in order to improve the handling of the surgical cutting device. An electrical contact is provided connectable to a current generator to deliver current to the cutting polypectomy snare.

Also known are snare devices having an injection device as especially disclosed in EP 0997 106 B1. This instrument comprises a snare directly connected to a distal end of an injection needle extending at the distal end of a catheter in a deployed position. This snare may also be provided as a monopolar cutting wire which may be delivered with a current for being able to cut a polypus by electrical current delivered through the wire. This prior art also discloses to cut a polypus only by the snare not being delivered with electrical current but constricting the polypus until it is cut from the rest of the tissue.

Further, as mentioned such a device for object retrieval should provide a loop which is adapted to easily encircle the object sought, and which provides for a more flexible engagement of the captured object, with the catheter, to allow the object to move during the retrieval process to circumnavigate tight spaces in the vascular system without harm. Since piercing of tissue might be required to reach a lost object, such a snare should preferably have structure to allow puncturing of tissue. Finally, such a device should have sufficient length to encircle any lost object, making it easy to capture.

Therefore, an object of this invention is the provision of a retrieval component for the capturing of objects, especially also tissue or inorganic components, from a human or animal body.

An additional object of this invention is the provision of such a retrieval component that is formed in memory imparted loop or snare.

Another object of this invention is to provide a snare device which can be used for securely grasping or capturing an object and for cutting a tissue without use of electrical current as well as a method for retrieving an object from a human or animal body and a method for cutting a tissue by use of such an improved snare device.

SUMMARY OF THE INVENTION

The problem is solved for a snare device for capturing an object and/or for cutting a tissue according to the preamble of claim 1 by providing a locking wire for being translated through the at least one loop to capture an object between part of the loop and the locking wire extending through the loop and/or for puncturing the tissue and/or for cutting the tissue by the loop as combined with the locking wire the locking wire piercing the tissue at a second aperture distant from a first aperture at least part of the loop extends through the locking wire being translated through the loop and engaging with the same and retracting the loop into the hollow member such that the tissue is cut between both of the apertures. The problem is also solved by providing two loops connected by twisting, one of the loops being the smaller one and one being the larger one and wherein the plane of the smaller loop is provided with an angle of about 120☐ to 170☐ to the axis of the hollow member and the plane of the larger loop is provided with an angle of about 10° to 60° to the plane of the smaller loop. Further, the problem is solved by providing two loops connected by twisting and a sheath, the sheath extending to the proximal end of the at least one loop, surrounding part of a wire or wires of the loop or loops and being angled or curved and the loops being deployable such that the smaller one extends between the halves of the larger loop. The problem is further solved by a method for retrieving an object from a human or animal body employing a snare device deployable from a hollow member, especially a catheter, and retractable into the hollow member, the snare device comprising a twisted loop with at least two loops and a twisted area connecting both loops when deployed in the side view the planes of the loops are angled one to the other and to the direction of the hollow member, and comprising a locking wire housed in the hollow member, comprising the steps of:—encircling the object by the curved area such that both loops are provided next to the object,—extending the locking wire through at least one of the loops,—retracting the loops into the hollow member such that the object is held between part of the loops and the locking wire, and—retracting the locking wire together with the loops and the held object into the hollow member. Further, the problem is also solved by a method for cutting a tissue by use of a snare device deployable from a hollow member, especially a catheter, and retractable into the hollow member, the snare device comprising a twisted loop having at least two loops and a twisted area connecting both loops when deployed in the side view the planes of the loops are angled or parallel one to the other and the twisted area is radially distant from the hollow member, and comprising a locking wire housed in the hollow member, comprising the steps of:—piercing the tissue with a first aperture and extending the at least one loop through the first aperture to place the twisted area generally within the first aperture,—piercing the tissue with a second aperture and extending the locking wire through the second aperture and through the at least one loop the locking wire extending as a prolongation of the hollow member,—retracting the at least one loop into the hollow member and thereby cutting the tissue with a cut between both apertures. Developments of the invention are defined in the dependent claims.

The foreign body capturing component or snare device, respectively, and system herein described and disclosed features a memory shaped wire snare or loop engaged to or made as one part with a translatable control wire and which is collapsible for translation through a conduit or a hollow member like a catheter, a sheath or a similar type device. The control wire engaged at or provided as one part with a first end of the snare runs to a surgeon-manipulatable actuator at a proximal end of the catheter allowing the surgeon to control the translation of the control wire and snare. The snare is likewise translatable and, thus, deployable from within the distal end of the catheter housing it, and, once so deployed, if not used to capture a loose object, may be translated or retracted, respectively, back into the axial cavity of the catheter from which it was deployed. One or more wires, especially two wires, may extend proximally from the proximal end of the at least one loop of the snare device and may be used as control wires to especially retract the loops into the hollow member, e.g. a catheter.

Preferably, two loops are provided one of which being the smaller one and one being the larger one the loops being connected via a twisting area. By providing such two loops connected by twisting an optimal extent of each of the loop parts or the newly built two loops—e.g. a smaller one and a larger one—is adjustable. In principle, both loops may also be essentially identical as regards their dimensions. The snare device or retrieval component, respectively, that may be provided as a kit of different shaped loops or snares may, thus, be employed with a hollow member, e.g. a catheter, having a locking wire common to all snares of the kit.

Preferably a sheath is provided extending to the proximal end of the at least one loop and surrounding the wire or wires. The sheath may be straight and/or angled and/or curved in a distal area. By being straight it is easy to push and direct the extended loops together with the sheath through the catheter. By being angled or curved it is possible to deploy the proximal loop not with an angle to the sheath which is the normal case with a straight sheath but as a prolongation of the angled or curved sheath. The shape of that loop may, thus, be changed.

It is further possible that two loops connected by twisting and a sheath are provided the sheath extending to the proximal end of the at least one loop, surrounding part of a wire or wires of the loop or loops and being angled or curved and the loops deploy such that the smaller one is the proximal one extending between the halves of the larger loop. It is still possible to extend a locking wire through the distal loop since this loop may extend in the direction of the sheath with its distal end. Further, a grasping or capturing of an object may be easier in hollow spaces of a human or animal body where a stiffer element than a loop is more comfortably placed and held in place during the grasping or capturing procedure. Furthermore, because of the deployment of the distal loop in the direction of the catheter and sheath, respectively, the dimension of such a snare device is smaller than in case the distal loop deploys away from the catheter and sheath in an angle to the proximal loop as described above. Therefore, such a snare device having a smaller dimension can excellently be used in small hollow spaces in a human or animal body especially for grasping or capturing objects.

Using the described techniques according to the present invention, the device may be employed in vascular procedures such as stent implantations, as well as in open surgeries, endoscope surgeries, or intrauterine therapies of complex cardiovascular diseases. Essentially it may be employed any surgery where retrieval of a lost object is required. In all such surgeries, the resulting retrieval of the loose object is handled with minimal invasive techniques. During deployment, as the loop is pushed from the distal end of the catheter, the memory shape material forming the curved or serpentine-shaped loop, will immediately begin to curve to its memorized shape. This curving effect may be employed to guide the snare to a wrap-around capture of the loose object. Once so captured, the locking wire is deployed from the distal end of the catheter and through the loop to hold it around the object as the loop or snare may be retracted into the catheter, especially by use of a control wire.

So engaged to the loop, the captured object will be somewhat flexibly engaged at the distal end of the catheter or generally the hollow member allowing it to move as the catheter is withdrawn. This means for hinge-like engagement, helps prevent injury to tissue if the captured object is elongated and traverse to the axis of the catheter.

The snare is pre-formed of shape memory material to form an encircling loop which may be placed in a fixed removable engagement around the object being retrieved by the or a further locking wire. It is, thus, an advantage of the present invention that such a snare device or engagement component, respectively, employs a unique wire locking system which allows for a flexible engagement at the distal end of the catheter during removal.

It is further advantageous to provide, when deployed, the plane of the smaller loop with an angle α of about 120° to 170°, especially about 150°, to the axis of the hollow member or the locking wire, respectively, for capturing of an object. The plane of the larger loop can advantageously be provided with an angle β of about 10° to 60°, especially about 30°, to the plane of the smaller loop for the capturing of an object. By such a configuration the snare device can encircle an object very securely and it is easy to further hold the object by use of the locking wire extending through the distal loop of the snare device, especially.

For cutting a tissue the plane of the smaller loop and the larger loop can be provided essentially parallel to one another to be placed on both surfaces of the tissue. It is then possible to define the length of the cut by the dimension of the loops, especially the smaller loop. The extent of the smaller loop between the distal end of the catheter or a sheath surrounding the proximal ends of the loop can be adapted or changed to define the length of the cut to be provided in the tissue. As just mentioned above, after puncturing the tissue by the snare and extending one loop on each side of the tissue and further puncturing the tissue by the locking wire and extending the same through the distal loop the loops are retracted into the hollow member, e.g. catheter. Thereby, the loops are pulled in the direction to the locking wire such that the tissue is cut from the puncturing opening the snare runs through to the puncturing opening the locking wire runs through.

The deployable snare features a memorized shape which will wrap around a lost or loose object in the body as the control wire translates the snare from the distal end of the catheter. Such a device should be easily deployed and viewed during the capture process and also during the above described cutting process. Therefore, it is advantageous to provide a marker at the loop, especially the smaller loop, for making the loop visible under visualization means. Visualization of the deploying snare component and resulting capture of a loose object would be possible by fluoroscope, or MRI, or other means for electronic visualization of the snare which can contain an x-ray's marker, echographic marker or magnetic resonance marker.

Further, as just described, the disclosed device has the additional benefit of being able to puncture through tissue adjacent to the distal end of the deployed catheter. This is accomplished by the leading edge of the loop being a pointed portion provided such that it can be used for puncturing the tissue. The pointed leading end on the snare projects from the distal end of the catheter first on deployment. A hole can thus be punched through tissue. Additionally, the device may be employed to cut tissue adjacent to the distal end of the deployed catheter. In this action, once the snare has pierced the tissue wall it folds or curves to an angle away from the axis of any control or locking wire or the catheter.

After puncturing the tissue wall by the pointed portion of the loop the locking wire can be projected from the catheter and pierce the tissue wall, as just described above, for cutting the tissue. A subsequent retraction of the loop, causes a cut in the tissue between the loop piercing the tissue, and the locking wire pierce point of the tissue.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description and following detailed description are considered as illustrative only for the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

These together with other objects and advantages which will become subsequently apparent reside in the details of the construction and operation as more fully hereinafter described and claimed, reference being had to the accompanying drawings forming a part thereof, wherein like numerals refer to like parts throughout the description.

As such, those skilled in the art will appreciate that the conception, upon which this disclosure is based, may readily be utilized as a basis for designing other methods and systems for carrying out the several purposes of the present invention of a loop or snare-based object retrieval system for surgery. It is important, therefore, that the claims be regarded as including such equivalent construction insofar as they do not depart from the spirit and scope of the present invention. The present invention provides these and other features that will be apparent upon review of the following.

BRIEF DESCRIPTION OF THE DRAWINGS

FIGS. 4A-9A show the capturing and grasping process of an object with the snare device according to FIGS. 2A-2H as a side view;

FIGS. 4B-9B show the capturing and grasping process of FIGS. 4A-9A in a front view;

DETAILED DESCRIPTION OF THE INVENTION

Figure 1A:
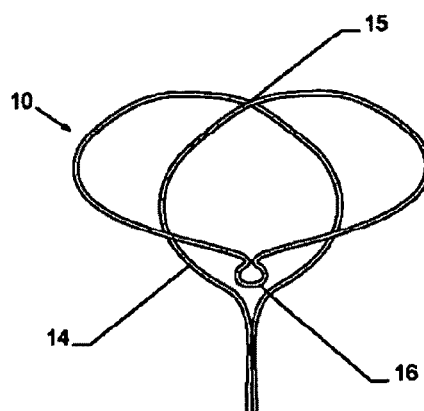
FIGS. 1A-1C show a first embodiment of a snare device according to the present invention as a perspective front view, as detail side view and in a top view, and with a control wire extending to a proximal loop twisted to a distal loop.

Before explaining at least one embodiment of the invention in detail it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Referring now to the drawings in FIGS. 1A-44C, wherein similar parts are identified by like reference numerals, there is seen generally in all of the figures a snare device 10 formed of a twisted loop of memory shaped material. On deployment from a catheter (not shown in FIGS. 1A-C), the memory shaped material forming the snare twists and contracts to form the shape as shown in the figures. The wire forming the snare twists and crosses over to form a smaller loop 14 and a larger loop 12. At least in the embodiment as shown in FIGS. 1A-2H at the leading edge of the larger loop 12 and the first component to translate from the catheter is a pointed portion 16. As noted, this pointed portion 16 may be employed to puncture tissue during deployment of the snare.

As shown in the front view of FIG. 1A the snare device 10 comprises a control wire 34 having two ends extending to the overlapping loops 12, 14 and provided of one part with the wire of these loops 12, 14 wherein the loops are provided at the distal end of the wire halves. The control wire 34 is provided for controlling the deployment and retracting of the snare device out of and into the catheter 26 being shown in FIGS. 2A-2H. The control wire 34 ends extend to the proximal end of the smaller loop 14 which is twisted at its distal end in area 15 to build the larger loop 12. At the distal end of the larger loop 12 the pointed portion 16 is provided.

Figure 1B:
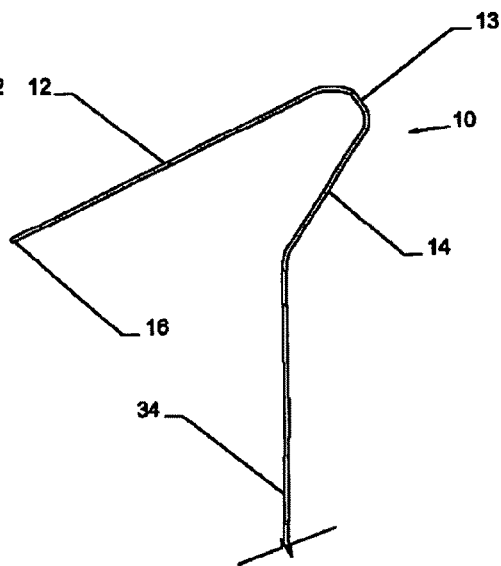
Figure 1C:
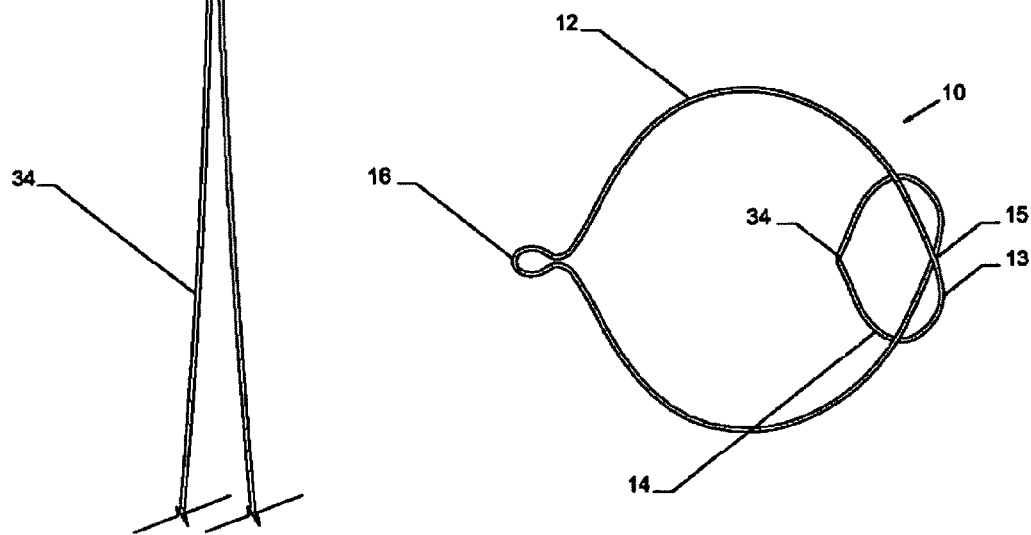
Figure 2A:
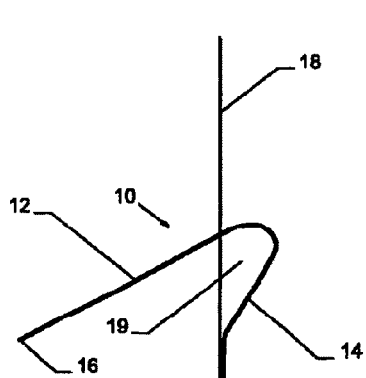
FIGS. 2A-2H show a side view and perspective side views, a top view and perspective top views, a perspective front view, and a detail side view of a second embodiment of a snare device according to the present invention provided with a locking wire.
Figure 2B:
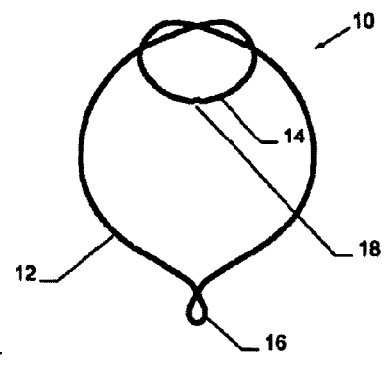
Figure 2C:
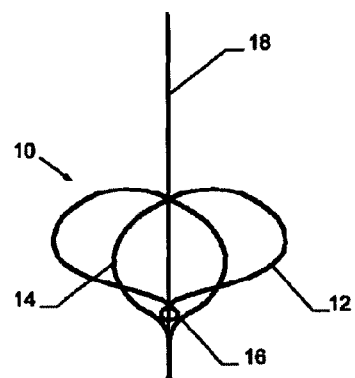
Figure 2D:
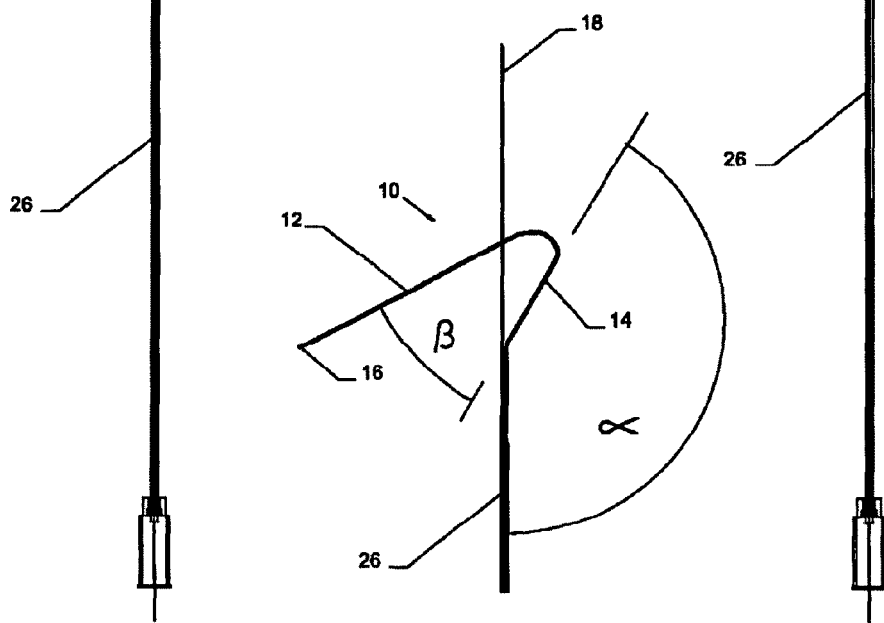
Figure 2E:
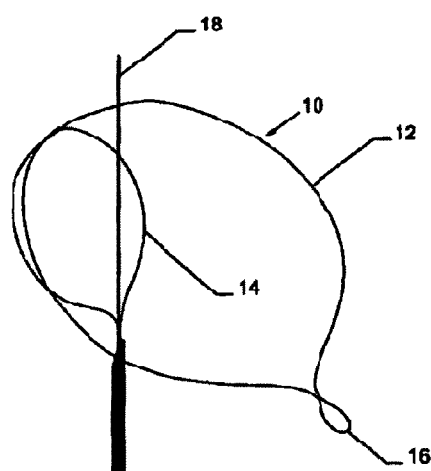
Figure 2F:
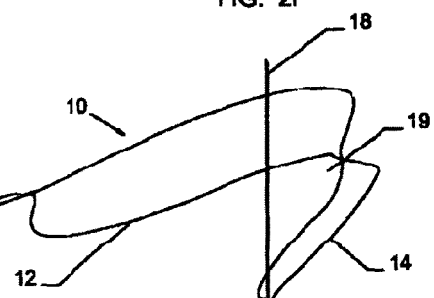
Figure 2G:
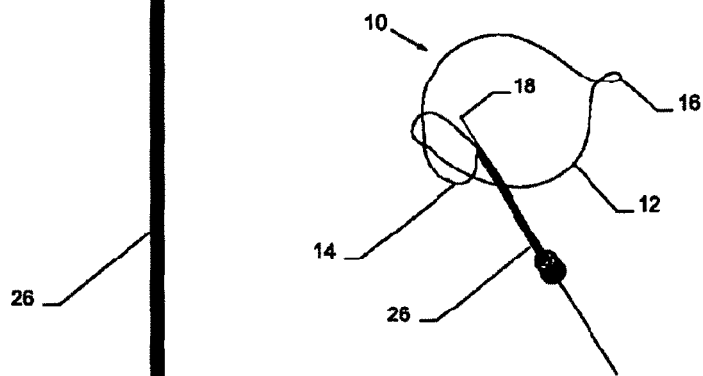
Figure 2H:
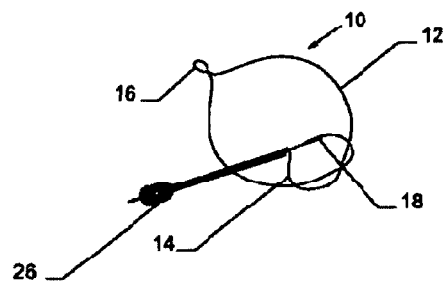

As may especially be seen from the detail side view in FIGS. 1B, 2A and 2D the loops 12, 14 have a snake or goose neck type shape where the smaller loop 14 is bent away from the longitudinal extent of the control wire 34 or the catheter 26, respectively, and the larger loop 12 is bent back to the opposite side. Thus, both loops as regarded in the side view or as regarding their planes after deployment are angled one to the other and to the longitudinal extent of the catheter 26 or the control wire 34. As may also be seen from these figures the loops 14 and 12 are connected by a curved section 13—in the side view—which means that the loops 14 and 12 are twisted and in addition bent or curved in that section 13. According to FIGS. 1A-C, this is also the section where the twisted area 15 is provided.

The twisting of the wires of both loops 14 and 12 may best be seen from the top view in FIG. 1C. From this figure also the specific shape of the pointed portion 16 may be seen which is built by the wire of loop 12 by forming a noose but not twisting the wires at the proximal end of the noose. According to this embodiment the noose extends in the same plane of loop 12 as may be seen from FIG. 1B. However, it is also possible that the noose extends angled to this plane.

Referring now to FIGS. 2A-2H, according to this embodiment of snare device 10 the control wire parts are provided in catheter 26 and the loops 12, 14 are shown in a deployed status being very similar or identical with the deployed status of the snare device as shown in FIGS. 1A-C. Especially FIG. 2D depicts an angle orientation of the snare device showing that the plane of the smaller or first loop 14 is angled to the longitudinal axis of the catheter 26 by angle $\alpha$ and that the plane of loop 14 is also angled to the plane of loop 12 by angle $\beta$. The angle $\alpha$ may be in the range of about 120° and 170° and the angle $\beta$ can be in the range of about 10° to 60°. Herewith it is meant that each and every value is possible for the angle between the catheter 26 and the plane of the loops 14 and 12, especially an angle of $\alpha$=150°, 149°, 148°, 147°, 146°, 145° etc. or 151°, 152°, 153°, 154°, 155° etc. and $\beta$=30°, 31°, 32°, 33°, 34°, 35° etc. or 29°, 28°, 27°, 26°, 25°, etc. Also an angle $\alpha$=150.15° or an angle of $\beta$=31.26° or any other angles are possible.

The main difference between FIGS. 1A-C and FIGS. 2A-H is that a locking wire 18 is provided in FIGS. 2A-2H extending through the catheter 26 in the direction of the longitudinal axis of the catheter. The loops 12, 14 are, thus, also angled to the locking wire 18. The locking wire 18 extends through the larger loop 12 only, defining a section 19 where an object can be captured between part of loop 12, loop 14 and the locking wire 18. This will be further explained with regard to FIGS. 4A to 9B.

In FIGS. 3A-3I another embodiment of the snare device is shown where the smaller loop 14 is the distal loop and the larger loop 12 is the proximal loop and where no pointed portion is provided. Further, a sheath 20 is provided surrounding the control wire ends of the loops. The sheath is helically wound around the control wire ends of the loops 12, 14. It is angled in its distal part such that the proximal larger loop 12 is automatically also angled to the longitudinal axis of the catheter without being shaped with such an angle itself. The loops may be adjusted by the sheath and/or by the control wire.

Figure 3A:
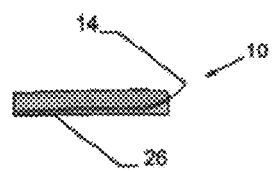
FIGS. 3A-3F show side views of the deployment of a third embodiment of a snare device according to the present invention.
Figure 3B:
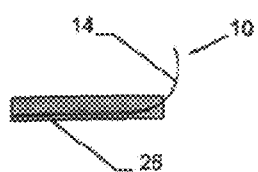
Figure 3C:
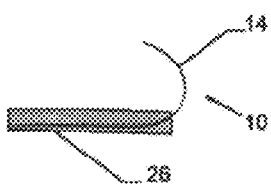
Figure 3D:
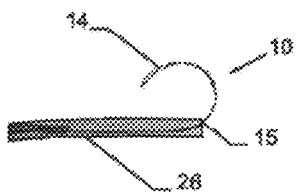
Figure 3E:
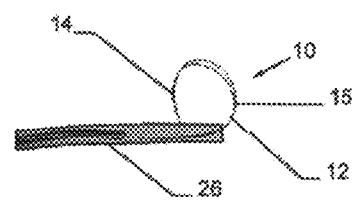
Figure 3F:
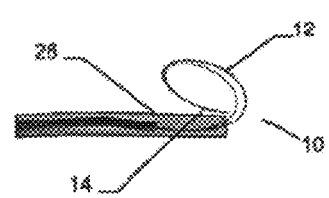
Figure 3G:
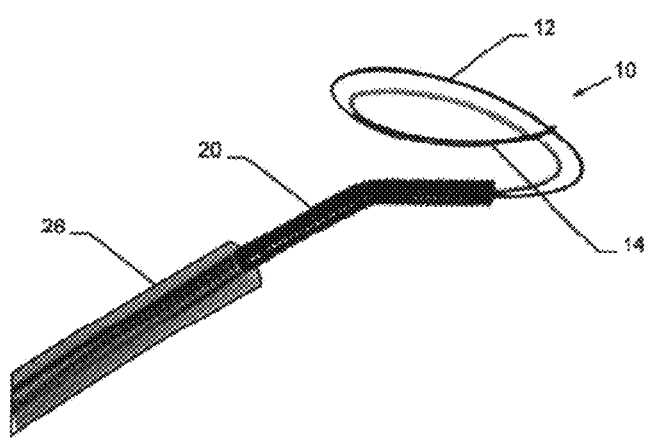
FIGS. 3G-3I show three perspective views of the snare device of the third embodiment as shown in the deployed status in FIG. 3F.
Figure 3H:
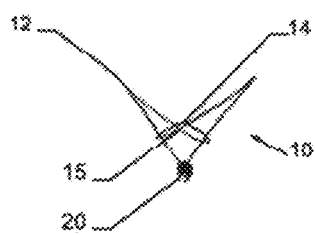
Figure 3I:
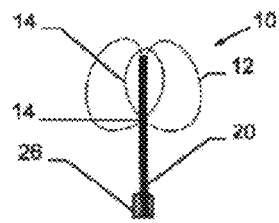
Figure 10:
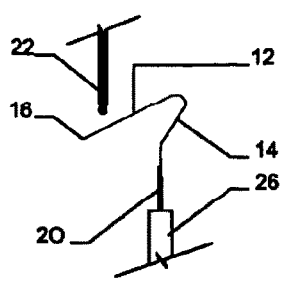
FIGS. 10-21 show the capturing and grasping process of an object with the snare device according to FIGS. 1A-C in side views.
Figure 11:
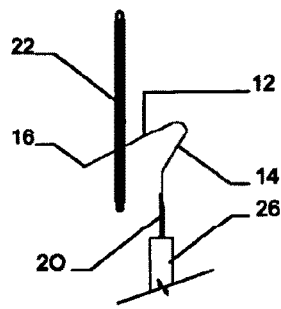
Figure 12:
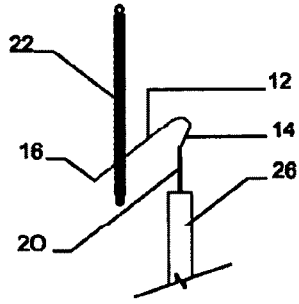
Figure 13:
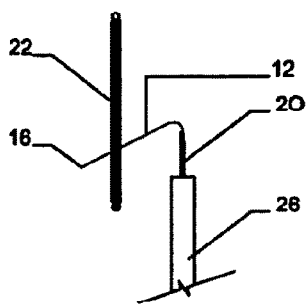
Figure 14:
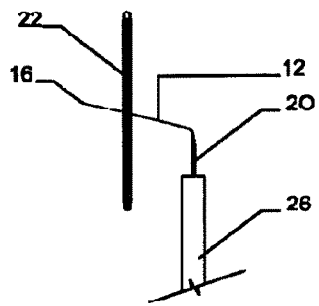
Figure 15:
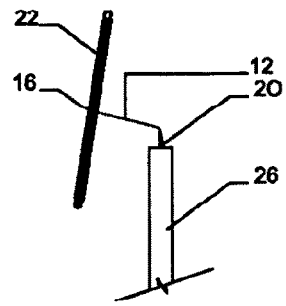
Figure 16:
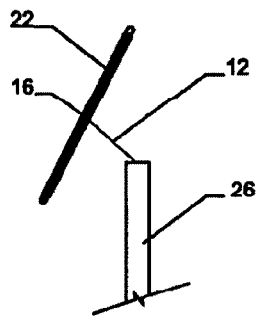
Figure 17:
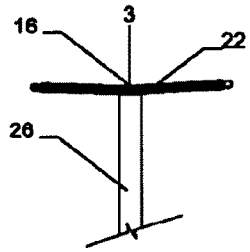
Figure 18:
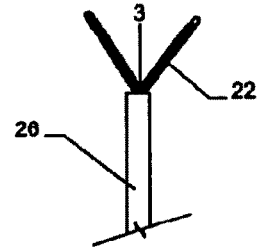
Figure 19:
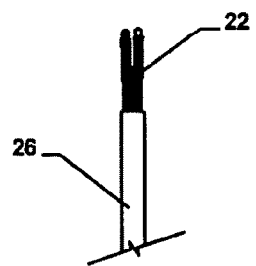
Figure 20:
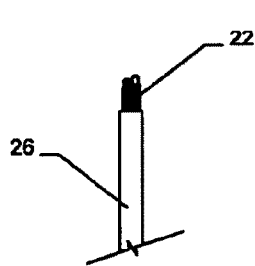
Figure 21:
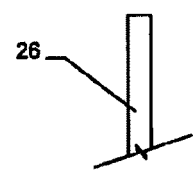

The distal smaller loop 14 deploys back to the sheath to extend partly parallel to the angled part of the sheath 20 as may best be seen from FIG. 3G. In the front view of the sheath in FIG. 3H it may be seen that the larger loop 12 opens in the shape of two "V"s and the smaller loop 14 also opens in an angled shape homologous to the "V"s of the larger loop 12. From the top view in FIG. 3I it is clear that in the top view the smaller loop 14 extends within the larger one and that the wire is twisted in the area of connection to the larger loop 12.

FIGS. 3A-F show the steps of deployment of this snare device 10, where it may be seen that first the distal end of the smaller loop 14 deploys out of the catheter 26. Afterwards the rest of the smaller loop 14 deploys (FIGS. 3B-3D) and also the twisted area 15. By further pushing the sheath 20 and the loops out of the catheter 26 also the larger loop 12 deploys, which may be seen in FIGS. 3E and 3F. The larger loop 12 in principle engages the distal end of the smaller loop 14 when both loops are deployed. The fully deployed shape of the snare device 10 may be seen in FIG. 3G.

FIGS. 4A to 9B show the capturing or grasping process of an object 22 by use of the snare device 10. The object 22 is shown as a longitudinal helically wound element having eyelets at both ends. The shown object is only one possible example for such an object which may be grasped from a human or animal body by use of the snare device 10. The object may have any other shape and dimension as well. The object is encircled or enveloped by the snare device being disposed between both loops 12, 14 as shown in the side view in FIG. 4A and in the front view in FIG. 4B. After encircling or enveloping the object by both loops 12, 14 the locking wire 18 is extended through deployed loop 12 to secure the object within built section 19. This step is shown in FIGS. 5A and 5B.

For removing or retrieving the object one (the surgeon) pulls on the sheath 20 or, in case no sheath is provided, on at least one of the two ends of the control wire 34. By pulling the loops into the catheter 26 the shape of the loops 12, 14 and the section 19 is amended and the snare device tightens around the object 22. This is shown in FIGS. 6A, 6B, 7A, and 7B.

The locking wire 18 prevents the distal end of loop 12, especially the pointed portion 16, from returning to the catheter axial cavity. If the axial cavity of the catheter 26 is of sufficient diameter, the object 22, may be retracted into the catheter 26 as depicted in FIGS. 8A and 8B. FIGS. 9A and 9B show the fully retracted status of the snare device where only the catheter 26 is shown. The object 22 when being retracted into the catheter 26 is folded such that the axial cavity within the catheter 26 needs to be at least double the diameter of the object 12 to be grasped.

The capturing process of an object by use of the snare device 10 may also be provided without use of the locking wire 18. The steps of such a grasping or capturing process are shown in FIGS. 10 to 21. Contrary to the process as shown in the preceding FIGS. 4A to 9B the object 22 is captured by the loop 12 where the loop plane is disposed essentially perpendicular to the object's extent. In the first step in FIG. 10 loop 12 is moved near the object 22 in order to surround the same by the loop as may be seen in FIG. 11. After surrounding the object 22 at one part the loops 12, 14 are retracted into the sheath 20 first and into the catheter 26 afterwards. When retracting loop 12 into the sheath 20 the angle between loop 12 and sheath 20 becomes larger such that the loop surrounds the object essentially at its center then as may be seen in FIGS. 14 to 17. The object 22 is then held at area 3 by the pointed portion 16 of loop 12. By further retracting the loops into the catheter 26 the object is folded at area 3 and retracted into the catheter until being fully removed especially from a hollow space in a human or animal body. These steps are shown in FIGS. 18 to 21.

Figure 22A:
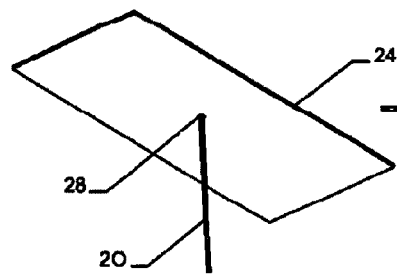
FIGS. 22A-44C show perspective views of the piercing and cutting an incision process of a tissue layer or wall by use of the snare device according to FIGS. 2A-2H.
Figure 22B:
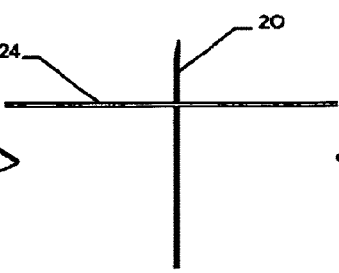
Figure 22C:
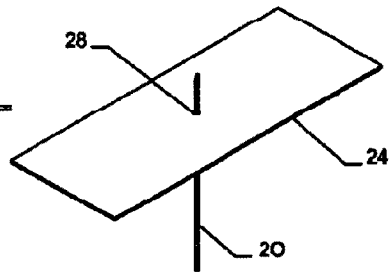
Figure 23A:
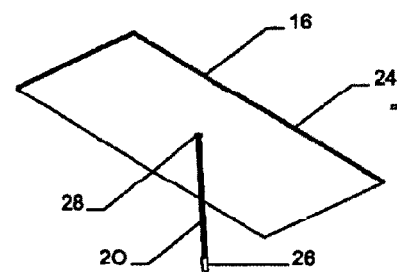
Figure 23B:
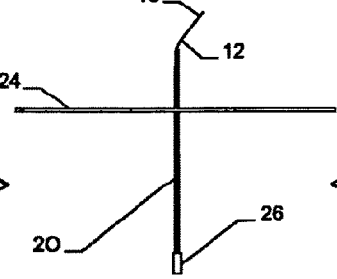
Figure 23C:
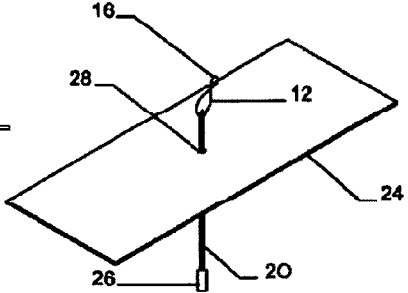

In another function provided by the unique two loop formation of the snare device comprising the locking wire 18, the device may be employed for both puncturing and cutting tissue as shown in FIGS. 22A-44C. As depicted in various modes of this operation, the catheter 26 and sheath 20 are maneuvered to a tissue wall 24 and the pointed portion 16 of the snare is projected from the distal end of the sheath 20 or catheter 26. This formed pointed portion 16 and the translation from the catheter 26 and the sheath 20 thereby provide a means for puncturing of tissue walls. Especially also the sheath 20 may be provided with a tapering distal end being able to puncture the tissue. FIGS. 22A-C show the puncturing step by use of the sheath 20 and the pointed portion 16 of loop 12. Thereafter the sheath 20 or the catheter 26 and/or the snare formed of the two loops 12 and 14, may be translated through an aperture 28 formed in the tissue wall 24 by the sheath 20 and the pointed portion 16.

Figure 24A:
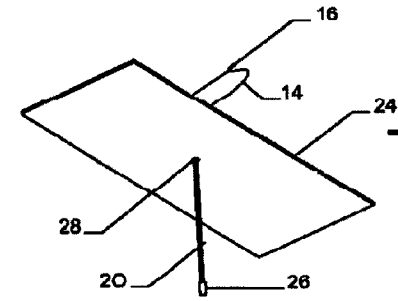
Figure 24B:
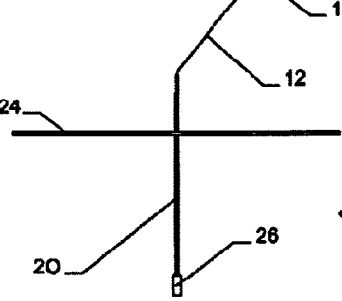
Figure 24C:
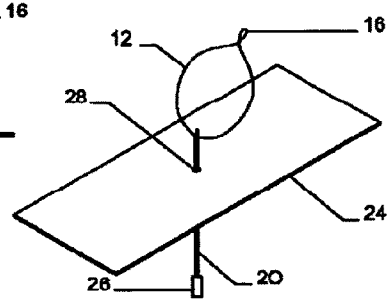
Figure 25A:
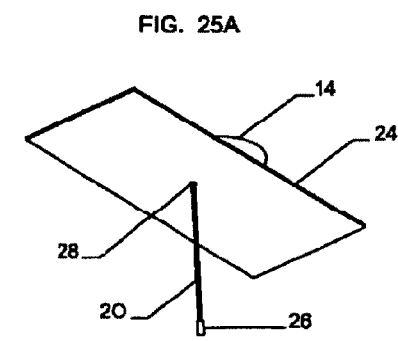
Figure 25B:
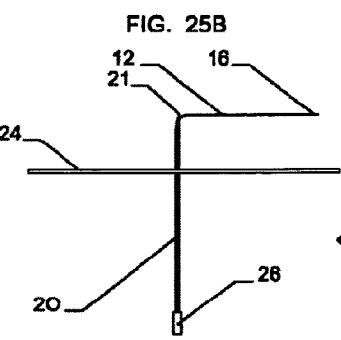
Figure 25C:
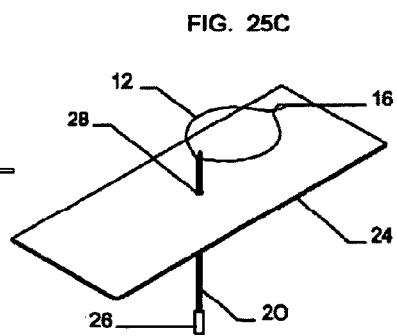
Figure 26A:
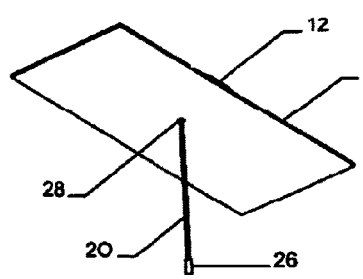
Figure 26B:
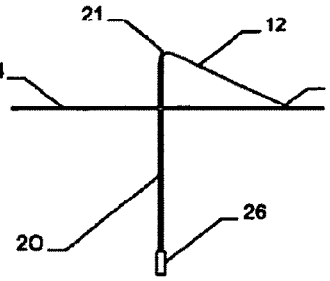
Figure 26C:
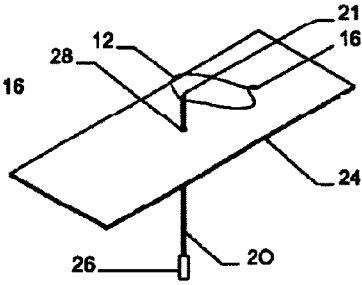

In a second operation, the device is employable for cutting an incision 32. In this operation, after the sheath 20 is passed through the aperture 28 the larger loop 12 of the snare is deployed on the opposite side of the tissue 24 as regards the catheter 26 starting with the pointed portion 16 of loop 12 (see FIGS. 23B-C). When deployed the plane of loop 12 first is provided in an angle to the sheath or catheter and to the tissue differing from about 90° as shown in FIGS. 24A-C. Afterwards, when loop 12 is further deployed the plane of loop 12 is essentially parallel to the plane of tissue 24 (see FIGS. 25A-C).

The distal end 21 of sheath is translated through the aperture 28 such that it is distant from the tissue surface. Because of the angle provided between the planes of loops 12 and 14 when further pushing loops 12 and 14 out of the sheath 20 or catheter 26 the plane of loop 12 is acute angled to the tissue plane. The pointed portion 16 of loop 12 may contact the tissue surface as may be seen from FIGS. 26B and 26C.

Figure 27A:
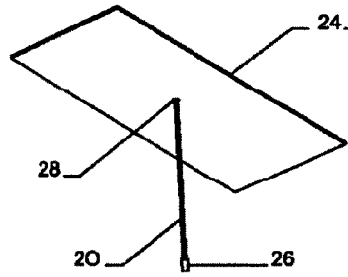
Figure 27B:
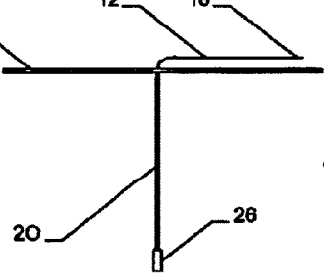
Figure 27C:
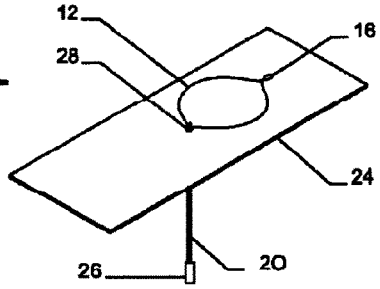
Figure 28A:
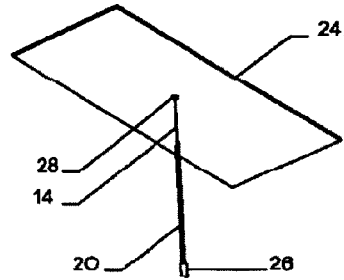
Figure 28B:
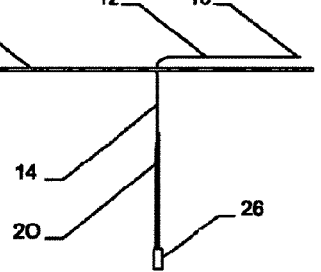
Figure 28C:
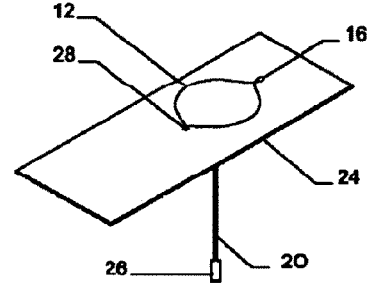
Figure 29A:
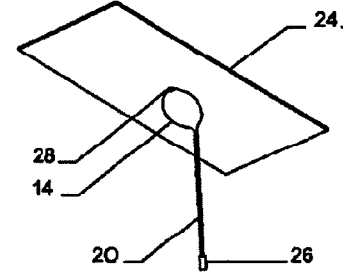
Figure 29B:
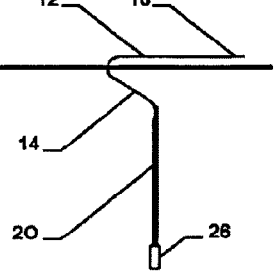
Figure 29C:
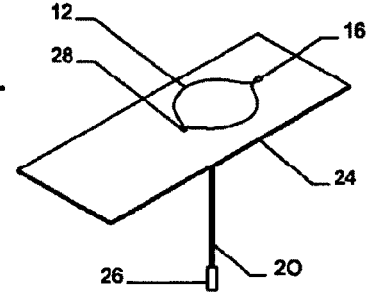

Afterwards sheath 20 is retracted through the aperture 28 back into catheter 26 such that plane of loop 12 will become parallel to the tissue surface again now having a small distance to the tissue surface, only (see FIGS. 27A-C).

When further pushing smaller loop 14 out of the sheath 20 or catheter 26 this loop deploys on the opposite side of tissue 24 with an angle to the tissue and to the plane of loop 12. The sheath 20 or catheter 26, respectively, is moved to a position such that loop 14 may deploy in its memorized shape. This position may be e.g. substantially centered as regards the larger loop 12 oriented perpendicular to the plane of the larger loop 12 resting on or above tissue 24. An easy means for measurement is provided by the smaller loop 14 which in the embodiment as shown in FIGS. 1A and 1B is approximately half the size of the larger loop 12.

Figure 30A:
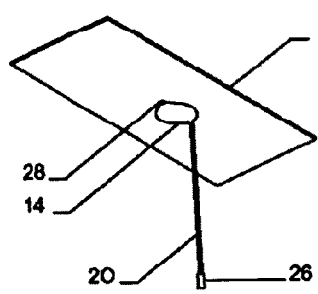
Figure 30B:
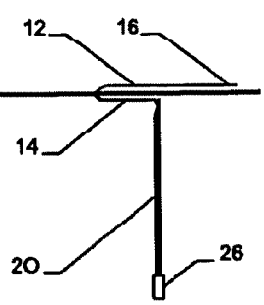
Figure 30C:
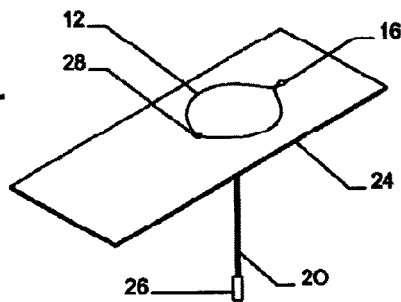
Figure 31A:
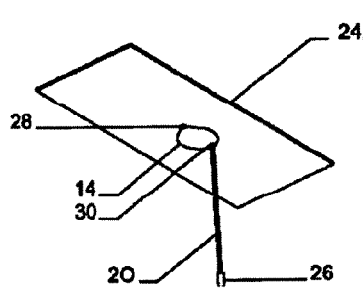
Figure 31B:
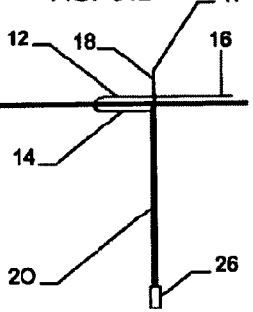
Figure 31C:
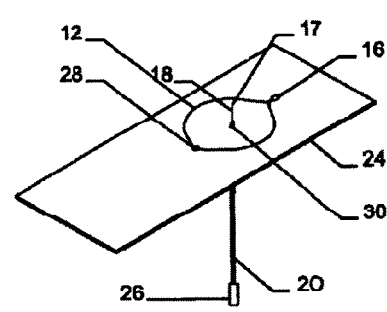
Figure 32A:
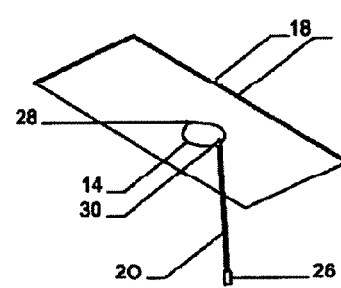
Figure 32B:
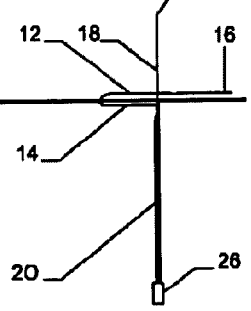
Figure 32C:
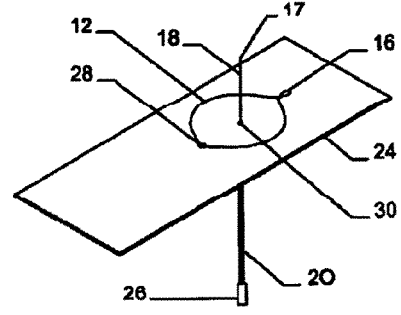
Figure 33A:
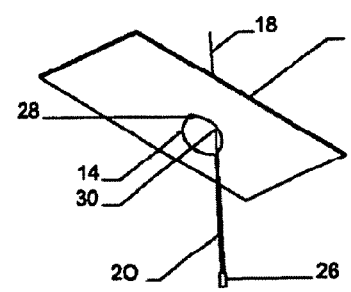
Figure 33B:
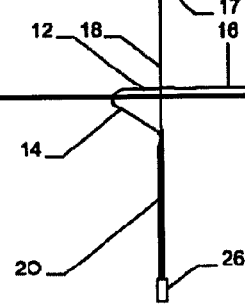
Figure 33C:
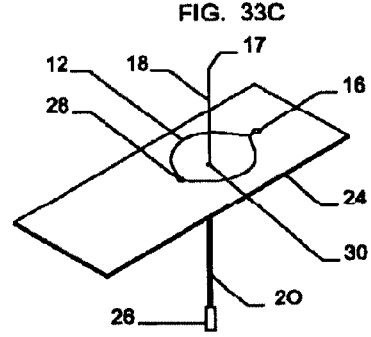
Figure 34A:
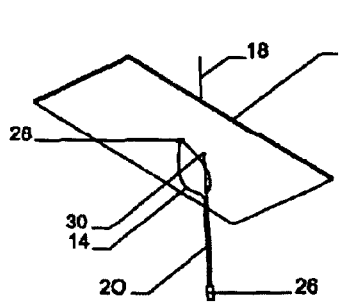
Figure 34B:
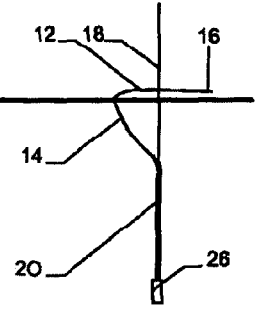
Figure 34C:
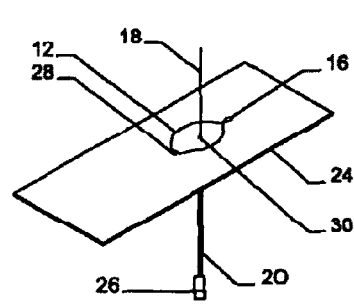

As shown in FIGS. 30A-C the sheath 20 is then pushed versus the tissue 24 such that both loops 12, 14 are provided essentially parallel to the tissue surface having only a small distance to the tissue surface.

Once so positioned, the locking wire 18 is translated toward and through the tissue 24 thereby puncturing a second aperture 30 through the tissue. The locking wire 18 is translated such that its distal end 17 projects past the tissue 24 as shown in FIGS. 31A-32C.

Figure 35A:
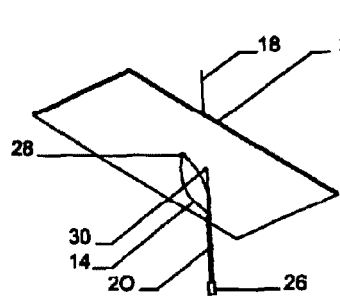
Figure 35B:
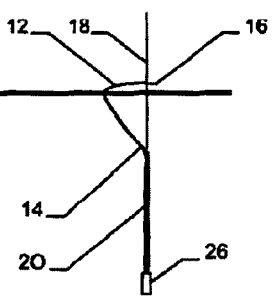
Figure 35C:
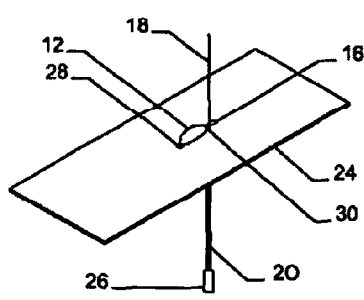
Figure 36A:
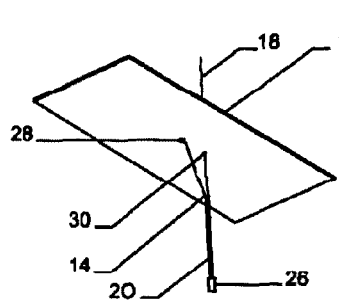
Figure 36B:
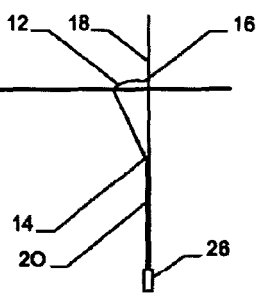
Figure 36C:
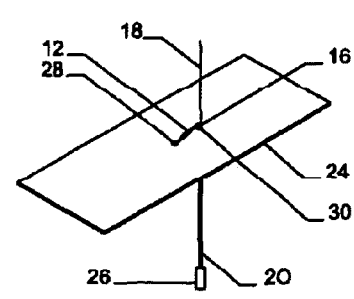
Figure 37A:
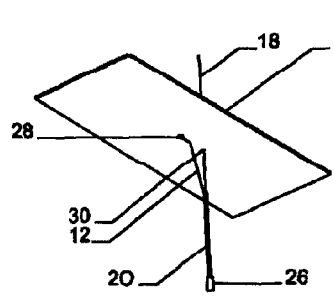
Figure 37B:
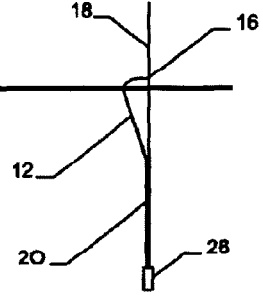
Figure 37C:
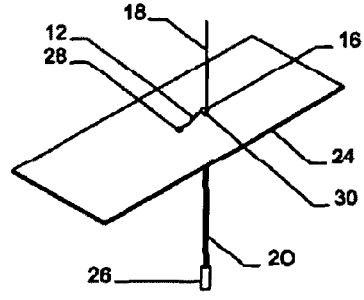
Figure 38A:
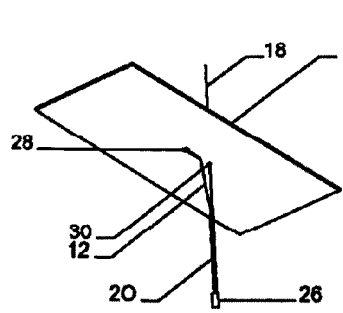
Figure 38B:
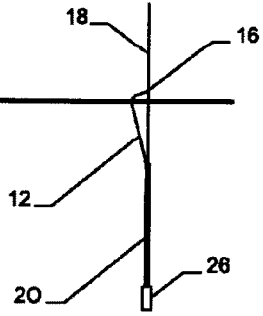
Figure 38C:
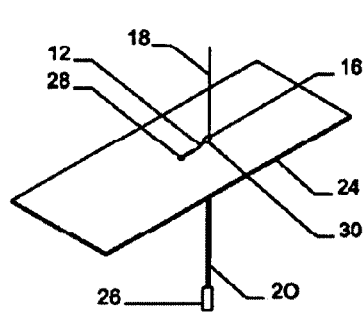
Figure 39A:
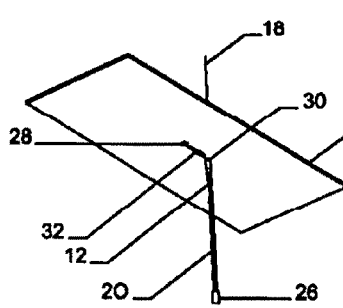
Figure 39B:
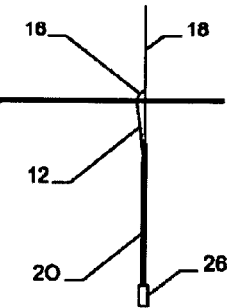
Figure 39C:
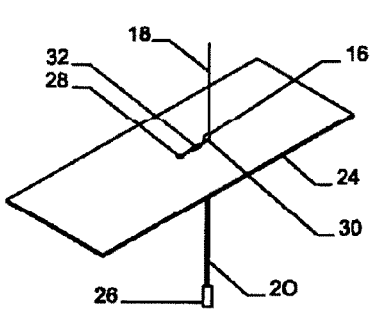
Figure 40A:
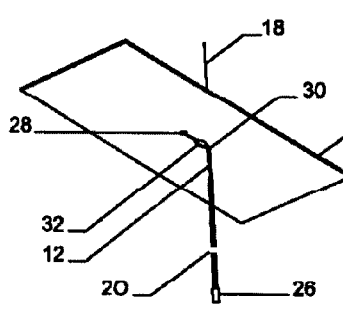
Figure 40B:
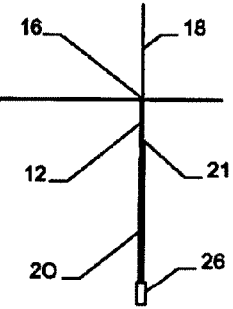
Figure 40C:
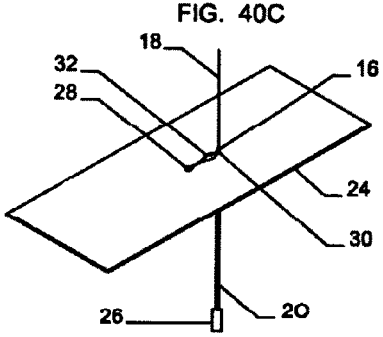

Thereafter, sheath 20 as well as possibly provided wire 34 for acting on the loops are translated back into the catheter 26 a distance. Thus, the plane of loop 14 is again angled to the tissue surface as may especially be seen from FIGS. 33A and 33B. By further retracting the loops into the sheath and catheter loop 12 will move over the tissue surface (FIGS. 35A-C). During this translation, the pointed portion 16 of the larger loop 12 will abut against the locking wire 18 stopping the translation progress. Both loops 12, 14 are stretched and they are pulled away from aperture 28 toward aperture 30 as may be seen in FIGS. 36A-37C.

Figure 41A:
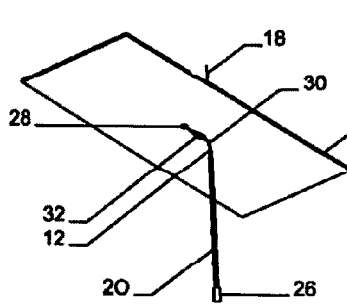
Figure 41B:
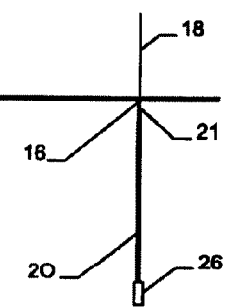
Figure 41C:
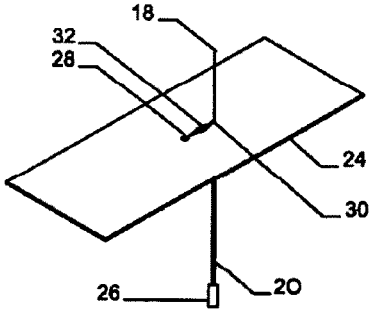
Figure 42A:
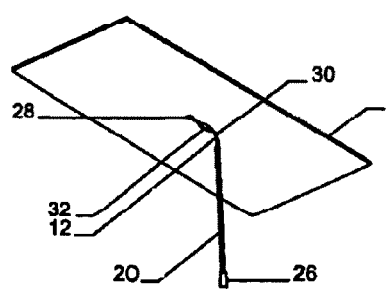
Figure 42B:
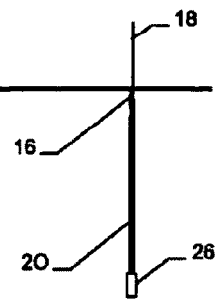
Figure 42C:
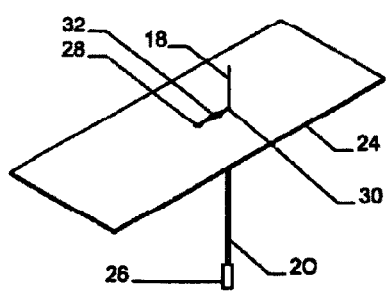
Figure 43A:
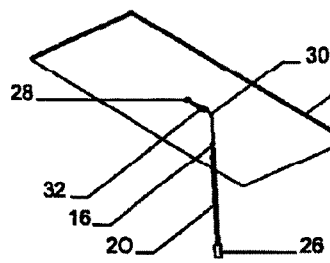
Figure 43B:
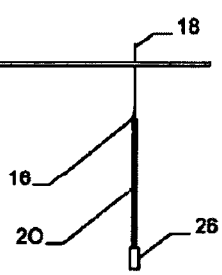
Figure 43C:
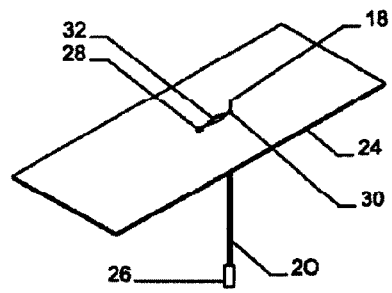
Figure 44A:
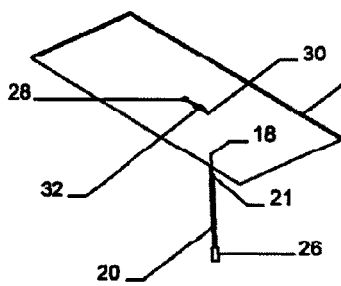
Figure 44B:
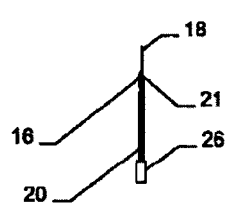
Figure 44C:
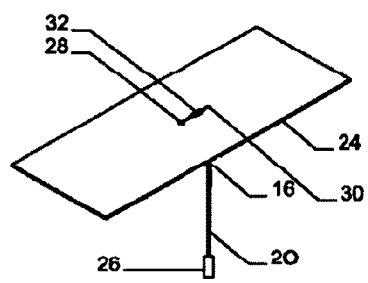

Subsequently, the force of wire 34 being pulled into the sheath 20 or catheter 26, respectively, will cause the wire forming the snare to cut an incision 32 between the first aperture 28 and the second aperture 30. This is step by step shown in FIGS. 38A-40C. The pointed portion 16 still encircles locking wire 18 and loop 12 extends parallel to the locking wire 18. By further retracting the loops into the sheath 20 the sheath is moved versus the tissue again until pointed portion 16 is fully pulled to the distal end 21 of the sheath on that side of the tissue (FIGS. 41A-C). After retracting the loops into the sheath also the locking wire 18 is retracted as shown in FIGS. 42A-44C. When retracting the locking wire 18 the pointed portion 16 of loop 12 is still positioned at the distal end 21 of sheath 20.

Once so cut, the device may be removed and the incision employed as necessary such as for communication of a larger surgical instrument therethrough.

A marker may be placed e.g. at the center portion of the smaller loop 14. The marker is visible using x-ray or fluoroscope, or other electronic means of visualization. This marker gives the surgeon a target to both wrap the serpentine snare around an object 22 to be grasped or captured, and also to employ the locking wire 18 into and through a portion of at least one of the loops 12 and 14, once the object 22 is encircled. To remove the object 22, once the locking wire 18 is deployed properly, the control wire or wires 34 communicating through the catheter to the snare are retracted. Two ends of wire 34 forming the loops and ending proximally at the surgeon are preferred in a continuous path forming the snare as this gives the surgeon the ability to pull upon either side of the snare during the capture of the object 22 and thus gives more options. Since the control wire 34 translates first through one of the loops forming the snare, as it is retracted, it will tighten around the object 22 being retrieved since the loop or loops contract around the object 22.

The method and components shown in the drawings and described in detail herein disclose arrangements of elements of particular construction and configuration for illustrating preferred embodiments of structure of the present snare for capture of objects and cutting of incisions in a human or animal body. It is to be understood, however, that elements of different construction and configuration, and using different steps and process procedures, and other arrangements thereof, other than those illustrated and described may be employed for providing a surgical retrieval device and method in accordance with the scope of protection as defined by the following claims.

As such, while the present invention has been described herein with reference to particular embodiments thereof, a latitude of modifications, various changes and substitutions are intended in the foregoing disclosure, and will be appreciated that in some instance some features of the invention could be employed without a corresponding use of other features, without departing from the scope of the invention as set forth in the following claims. All such changes, alternations and modifications as would occur to those skilled in the art are considered to be within the scope of this invention as broadly defined in the appended claims.

Further, the purpose of the abstract of the invention, is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting, as to the scope of the invention in any way.

REFERENCE NUMERALS 3 area
10 snare device
12 larger loop
13 curved section
14 smaller loop
15 twisted area
16 pointed portion
17 distal end of locking wire
18 locking wire
19 section
20 sheath
21 distal end
22 object
24 tissue wall
26 catheter
28 aperture
30 aperture
32 incision
34 control wires

What is claimed is:

1. A snare device for capturing an object, comprising:
a wire of memory shaped material shaped to define at least a first loop in a first plane and a second loop in a second plane so as to define a first region between said first and second loops, said wire being movable relative to a hollow member such that said first and second loops are deployable from and retractable into said hollow member; and
a locking wire translatable through at least one of said first and second loops after an object is encircled or enveloped by said first and second loops, so as to capture said object within said first region;
wherein:
said first region tightens around said object as said first and second loops are retracted into said hollow member; and
when said wire of memory shaped material is deployed from said hollow member, the first plane is angled relative to an axis of the hollow member or said locking wire by an angle α ranging from 120° to 170°, and the second plane is angled relative to the first plane by an angle β ranging from 10° to 60°.

2. The device as claimed in claim 1, wherein said hollow member is a catheter.

3. The device as claimed in claim 1, wherein said first loop is smaller than said second loop.

4. The device as claimed in claim 1, wherein said angle α is about 150°.

5. The device claimed in claim 1, wherein said angle β is about 60°.

6. The device as claimed in claim 1, wherein a leading edge of said second loop comprises a pointed portion configured to puncture tissue.

7. The device as claimed in claim 1, wherein said wire of memory shaped material further comprises a marker that is visible with electronic visualization means.

8. The device of claim 1, wherein said locking wire is substantially straight.

9. The device of claim 1, wherein:
said wire and said locking wire are retractable into said hollow member; and
prior to retraction into said hollow member, said locking wire is substantially straight.

10. A snare device for cutting a tissue, comprising:
a wire of memory shaped material twisted to define at least a first loop and a second loop, said wire being movable relative to a hollow member such that said first and second loops are deployable from and retractable into said hollow member; and
a locking wire translatable through at least one of said first and second loops; wherein:
said wire is distally translatable from said hollow member so as to dispose at least one of said first and second loops through a first aperture in said tissue, at least one of said loops being translatable over a surface of said tissue when said first and second loops are at least partially retracted into said hollow member;
said locking wire is distally translatable from said hollow member so as to extend at least a distal portion of said locking wire through a second aperture in said tissue after at least one of said first and second loops is disposed through said first aperture, so as to stop translation of one or more of said loops over said surface of said tissue;
said distal portion of said locking wire is operable to engage at least one of said first and second loops while it is extended through said second aperture; and
when said distal portion of said locking wire is engaged with at least one of said first and second loops, said locking wire and said first and second loops are operable in combination to cut said tissue by retracting said first and second loops into said hollow member.

11. The device as claimed in claim 10, wherein said hollow member is a catheter.

12. The device as claimed in claim 10, wherein to cut said tissue, said first loop and said second loop are deployed such that a first plane of said first loop and a second plane of said second loop are positioned substantially parallel to one another and adjacent to opposing sides of said tissue.

13. The device as claimed in claim 10, wherein said first loop is adjustable to define a length of a cut to be formed in said tissue.

14. The device as claimed in claim 10, wherein a leading edge of said second loop comprises a pointed portion configured to puncture said first aperture in said tissue.

15. The device as claimed in claim 10, wherein said wire of memory shaped material further comprises a marker that is visible with electronic visualization means.

16. The device of claim 10, wherein said locking wire is substantially straight.

* * * * *